United States Patent
Schmidt et al.

(12)

(10) Patent No.: US 6,368,679 B1
(45) Date of Patent: Apr. 9, 2002

(54) FERROELECTRIC LIQUID-CRYSTAL DISPLAY HAVING ACTIVE MATRIC ELEMENTS

(75) Inventors: Wolfgang Schmidt, Köln; Hans-Rolf Dübal, Eltville, both of (DE)

(73) Assignee: Aventis Research & Technologies GmbH & Co. KG, Frankfurt (DE)

( * ) Notice: Subject to any disclaimer, the term of this patent is extended or adjusted under 35 U.S.C. 154(b) by 0 days.

(21) Appl. No.: 09/463,370

(22) PCT Filed: Jul. 21, 1998

(86) PCT No.: PCT/EP98/04548

§ 371 Date: May 1, 2000

§ 102(e) Date: May 1, 2000

(87) PCT Pub. No.: WO99/05238

PCT Pub. Date: Feb. 4, 1999

(30) Foreign Application Priority Data

Jul. 25, 1997 (DE) .......................... 197 32 381

(51) Int. Cl.⁷ ..................... C09K 19/02; C09K 19/52; C09K 19/42

(52) U.S. Cl. ................... 428/1.1; 252/299.01

(58) Field of Search ................. 252/299.01, 299.61; 428/1.1

(56) References Cited

U.S. PATENT DOCUMENTS 5,767,924 A * 6/1998 Hiroki et al. ................ 349/5

FOREIGN PATENT DOCUMENTS

| EP | 0032362 | 7/1981 |
|----|---------|--------|
| EP | 0592092 | 4/1994 |
| EP | 0694599 | 1/1996 |
| EP | 0717305 | 6/1996 |
| WO | 96/15092 | 5/1996 |
| WO | 97/12355 | 4/1997 |

OTHER PUBLICATIONS

CAPLUS 1992: 71952.*

* cited by examiner

*Primary Examiner*—Shean C. Wu
(74) *Attorney, Agent, or Firm*—Frommer Lawrence & Haug LLP

(57) ABSTRACT

A ferroelectric active-matrix liquid-crystal display containing a ferroelectric liquid crystal which forms a 'spontaneous bookshelf' geometry.

3 Claims, No Drawings

FERROELECTRIC LIQUID-CRYSTAL DISPLAY HAVING ACTIVE MATRIC ELEMENTS

CROSS-REFERENCES TO RELATED APPLICATIONS

This application is an application filed pursuant to 35 USC § 371 from PCT application PCT/EP98/04548, filed on Jul. 21, 1998, which in turn claims priority to German application 197 32 381.2, filed Jul. 25, 1997.

STATEMENT REGARDING FEDERALLY SPONSORED RESEARCH OR DEVELOPMENT

Not applicable.

BACKGROUND OF THE INVENTION

1. Field of the Invention

This invention provides for ferroelectric liquid-crystal displays having active matrix elements.

2. Description of the Related Arts

In addition to nematic and cholesteric liquid crystals, optically active tilted smectic (ferroelectric) liquid crystals have also been used recently in commercial display devices.

Clark and Lagerwall have been able to show that the use of ferroelectric liquid crystals (FLCs) in very thin cells results in opto-electrical switching or display elements which have response times which are faster by a factor of up to 1000 compared with conventional TN ("twisted nematic") cells (see, for example, EP-A 0 032 362). On the basis of this and other favorable properties, for example the possibility of bistable switching and the virtually viewing angle-independent contrast, FLCs are fundamentally highly suitable for areas of application such as computer displays.

The use of FLCs in electro-optical or fully optical components requires either compounds which form tilted or orthogonal smectic phases and are themselves optically active, or the induction of ferroelectric smectic phases by doping compounds which, although forming such smectic phases, are not themselves optically active, with optically active compounds. The desired phase should be stable over the broadest possible temperature range.

The individual pixels of an LC display are usually arranged in an x,y matrix formed by the arrangement of a series of electrodes (conductor tracks) along the rows and a series of electrodes along the columns on the upper or lower side of the display. The points of intersection of the horizontal (row) electrodes and the vertical (column) electrodes form addressable pixels. The arrangement of the pixels is usually referred to as a passive matrix. For addressing, various multiplex schemes have been developed, as described, for example, in Displays 1993, Vol. 14, No. 2, pp. 86–93, and Kontakte 1993 (2), pp. 3–14. Passive matrix addressing has the advantage of simpler production and consequently lower production costs, but the disadvantage that passive addressing can only be carried out line by line, which results in the addressing time for the entire screen with N lines being N times the line addressing time. For usual line addressing times of about 50 microseconds, this means a screen addressing time of about 60 milliseconds in, for example, the HDTV (high definition TV, 1152 lines) standard, i.e. a maximum frame frequency of about 16 Hz, too slow for moving images. In addition, display of gray shades is difficult. At the FLC Conference in Brest, France (Jul. 20–24, 1997, see Abstract Book), a passive FLC display with digital gray shades was shown in which each of the RGB pixels (RGB=red, green, blue) was divided into sub-pixels, allowing the display of gray shades in digital form through partial switching. The disadvantage of this method is the considerable increase in the number of screen drivers necessary and thus in the costs (in the case of the above display, three times the number of drivers are necessary than in a standard FLC display without digital gray shades).

In so-called active matrix technology (AMLCDs), a non-structured substrate is usually combined with an active-matrix substrate. An electrically non-linear element, for example a thin-film transistor, is integrated into each pixel of the active-matrix substrate. The nonlinear elements can also be diodes, metal-insulator-metal and similar elements, which are advantageously produced by thin-film processes and are described in the literature (see, for example, T. Tsukuda, TFT/LCD: Liquid Crystal Displays Addressed by Thin-Film Transistors, Gordon and Breach, 1996, ISBN 2-919875-01–9, and the references cited therein).

Active-matrix LCDs are usually operated with nematic liquid crystals in TN (twisted nematics), ECB (electrically controlled birefringence), VA (vertically aligned) or IPS (in-lane switching) mode. In each case, the active matrix generates an electric field of individual strength on each pixel, producing a change in alignment and thus a change in birefringence, which is in turn visible in polarized light. A severe disadvantage of this process is the poor video capability, i.e. excessively slow response times, of nematic liquid crystal.

For this reason amongst others, liquid-crystal displays based on a combination of ferroelectric liquid-crystal materials and active-matrix elements have been proposed, for example in WO 97/12355, Ferroelectrics 1996, 179, 141–152, or W. J. A. M. Hartrmann (dissertation, Eindhoven, 1992).

In the latter case, a combination of the so-called 'quasi-bookshelf geometry' (QBG) of an FLC and a TFT (thin-film transistor) active matrix is utilized and thus a high response speed, gray shades and high transmission are achieved simultaneously. However, the QBG is not stable over a broad temperature range, since the temperature dependence of the smectic layer thickness disrupts or rotates the field-induced layer structure.

Although the commercialized 'chevron' geometry (C1 or C2) used in commercial FLC displays has adequate temperature stability, it does not have sufficient brightness, since the effective tilt angle is well away from its optimum value.

SUMMARY OF THE INVENTION

The invention relates to an active-matrix liquid-crystal display (LCD) containing a ferroelectric liquid crystal which forms a 'spontaneous bookshelf' (SBG) geometry. This is not, as in the QBG, generated by application of electric fields and thus temperature-unstable, but, by contrast, is stable over a broad temperature range.

The SBG is formed according to the invention in the temperature region of the $S_c^*$ phase. For a definition of 'bookshelf' and 'spontaneous bookshelf' geometry, see, for example, J. W. Goodby et al, Ferroelectric Liquid Crystals, Gordon & Breach, Philadelphia, 1992, "Introduction to Ferroelectric Liquid Crystals", and Mizutani et al in Conference Summaries, 6th Int. Conference on Ferroelectric Liquid Crystals, Brest, 1997, page 66.

The invention likewise relates to a ferroelectric active-matrix liquid-crystal display containing a ferroelectric liquid crystal, where the liquid crystal comprises one or more mesogenic compounds and where these mesogenic compounds contain a cyclic structure comprising two or more ring compounds and one or two side chains, wherein at least one mesogenic compound has at least one partially or perfluorinated side chain.

The ferroelectric active-matrix liquid-crystal display according to the invention is highly practicable, since it combines high transmission, a short response time, gray shades and a broad temperature range with one another.

Furthermore, the active-matrix FLC display according to the invention does not exhibit any 'zig-zag' deformations, or if it does, they are so slight that they are unimportant.

BRIEF DESCRIPTION OF THE DRAWINGS

Not applicable.

DETAILED DESCRIPTION OF THE INVENTION

Displays employed in accordance with the invention have a substantially vertical, i.e. non-chevron smectic layer structure and a high effective tilt angle of greater than 15°, and thus have high brightness and high contrast. In addition, such displays can advantageously have electrode separations of, in general, from 1 to 4 μm, preferably at least 1.5 μm, particularly preferably at least 1.8 μm, and can nevertheless be switched at voltages of ≦40 volts, preferably ≦30 V, particularly preferably ≦15 V, especially ≦10 V.

The spontaneous polarization of the active-matrix FLCD according to the invention is less than 100 $nC/cm^2$, preferably in the range from 0.1 to 30 $nC/cm^2$, particularly preferably from 0.5 to 15 $nC/cm^2$, especially in the range from 1 to 9 $nC/cm^2$, at the operating temperature of the display, i.e. preferably at 30° C.

Preference is given, in particular, to active-matrix FLCDs having a 'layer-leaning angle' of less than 10°, a spontaneous polarization of from 1 to 9 $nC/cm^2$, a switching angle (twice the tilt angle) of 35–55° and containing at least two mesogenic structures of the formula (I).

Preference is also given, in particular, to polysilicone active-matrix FLCDs having a layer-leaning angle of less than 10°, a spontaneous polarization of from 0.1 to 30 nanocoulombs per square centimeter, a switching angle (twice the tilt angle) of 35–55° and containing at least two mesogenic structures of the formula (I).

Particular preference is given to active-matrix FLCDs having a layer-leaning angle of less than 10°, a spontaneous polarization of from 1 to 9 nanocoulombs per square centimeter, a switching angle (twice the tilt angle) of 35–55° and containing an FLC mixture having at least 10 components, of which at least five are mesogenic structures of the formula (I) which, taken together, make up a total proportion by weight of 30% of the mixture.

For the purposes of the invention, 'mesogenic' means that the compound, alone or as a mixture with other mesogenic compounds, forms a liquid-crystal phase, preferably a ferroelectric phase.

Preferred mesogenic compounds having a partially or perfluorinated side chain are those of the formula (I)

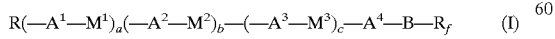

where the symbols and indices are defined as follows:
R is
a) hydrogen, —F, —Cl, —$CF_3$, —$OCF_3$ or —CN,
b) a straight-chain or branched alkyl radical (with or without an asymmetrical carbon atom) having 1 to 20 carbon atoms, where b1) one or more non-adjacent and non-terminal $CH_2$— groups may be replaced by —O—, —S—, —CO—, —CO—O—, —O—CO—, —O—CO—O— or —Si($CH_3$)$_2$—, and/or b2) one or more $CH_2$- groups may be replaced by —CH=CH—, —C≡C—, cyclopropane-1,2-diyl, 1,4-phenylene, 1,4-cyclo-hexylene or 1,3-cyclopentylene, and/or b3) one or more H atoms may be replaced by F, CN and/or Cl, and/or b4) the terminal $CH_3$ group may be replaced by one of the following chiral groups (optically active or racemic):

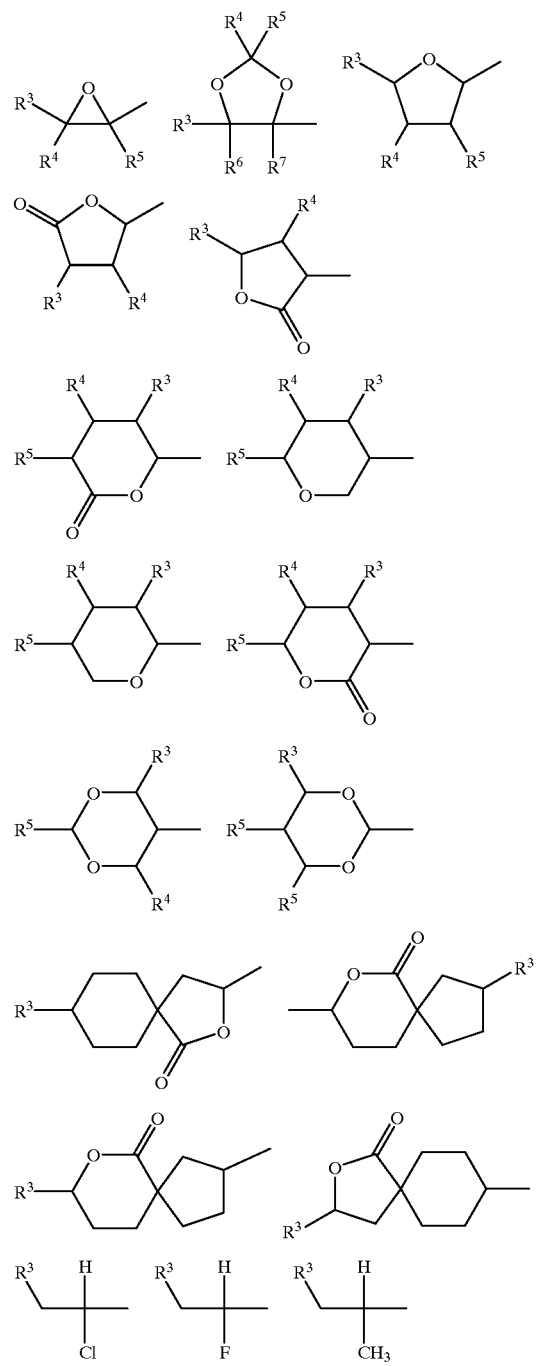

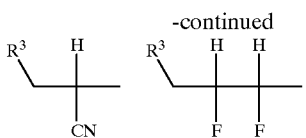

-continued c) B-$R_f$ $R^3$, $R^4$, $R^5$, $R^6$ and $R^7$ are identical or different and are
  a) hydrogen
  b) a straight-chain or branched alkyl radical (with or without an asymmetrical carbon atom) having 1 to 16 carbon atoms, where
    b1) one or more non-adjacent and non-terminal $CH_2$— groups may be replaced by —O—, and/or
    b2) one or two $CH_2$— groups may be replaced by —CH═CH—,
  c) $R^4$ and $R^5$ together may alternatively be —$(CH_2)_4$— or —$(CH_2)_5$— if they are bonded to an oxirane, dioxolane, tetrahydrofuran, tetrahydropyran, butyrolactone or valerolactone system;

$R_f$ is
  a straight-chain or branched, partially or perfluorinated alkyl radical (with or without an asymmetrical carbon atom) having 1 to 20 carbon atoms, where
    a) one or more non-adjacent and non-terminal $CH_2$— or $CF_2$-groups may be replaced by —O—, —S—, —CO—, —CO—O—, —O—CO—, —O—CO—O— or —Si(CH$_3$)$_2$—, and/or
    b) one or more CH2— or CF2— groups may be replaced by —CH═CH—, —C≡C—, cyclopropane-1,2-diyl, 1,4-phenylene, 1,4-cyclohexylene or 1,3-cyclopentylene;

B is
  —O—, —S—, —$(CH_2)_{n+1}$—O—, —O—$(CH_2)_{n+1}$—, —$(CH_2)_{n+1}$—S—, —S—$(CH_2)_{n+1}$—. —CO—$(CH_2)_n$—, —CO—O—$(CH_2)_n$—, —O—CO—$(CH_2)_n$—, —CO—S—$(CH_2)_n$—, —S—CO—$(CH_2)_n$—, —CS—O—$(CH_2)_n$—, —O—CS—$(CH_2)_n$—, —$SO_2$—$(CH_2)_n$—, —$OSO_2$—$(CH_2)_n$—, —CH═CH—, —C≡C—, —$(CH_2)_{n+1}$—, —CH═N—, —N($C_kH_{2k+1}$)—$(CH_2)_n$—N($C_kH_{2k+1}$)—CO—, —$(CH_2)_n$—N($C_kH_{2k+1}$)—$SO_2$—, —O—$[(CH_2)_{m+1}$—O$]_l$—$(CH_2)_n$—, —$[(CH_2)_{m+1}$—O$]_l$—$(CH_2)_n$— or a single bond;

m and n are identical or different and are, independently of one another, an
  integer from 0 to 15, k is an integer from 0 to 4, and l is an integer from 1 to 6, with the proviso that m+n≦15;

$M^1$, $M^2$ and $M^3$ are identical or different and are
  —CO—O—, —O—CO—, —CO—S—, —S—CO—, —CS—O—, —O—CS—, —CS—S—, —S—CS—, —$CH_2$—O—, —O—$CH_2$—, —$CH_2$—S—, —S—$CH_2$—, —$CH_2$—$CH_2$—, —CH═CH—, —C≡C—, —$CH_2$—$CH_2$—CO—O—, —O—CO—$CH_2$—$CH_2$—, —CH═N— or a single bond;

$A^1$, $A^2$, $A^3$ and $A^4$ are identical or different and are
  1,4-phenylene, in which one or more H atoms may be replaced by F, Cl, $CH_3$, $C_2H_5$, $OCH_3$, $CF_3$, $OCF_3$ and/or CN, 1,3-phenylene, in which one or two CH groups may be replaced by N, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, 1,4-cyclohexylene, in which one or two H atoms may be replaced by CN and/or $CH_3$ and/or F, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4-diyl, in which one H atom may be replaced by F, Cl and/or CN, thiophene-2,5diyl, in which one or two H atoms may be replaced by F, Cl and/or CN, naphthalene-2,6diyl, naphthalene-1,4-diyl or naphthalene-1,5-diyl, in each of which one or more H atoms may be replaced by F, Cl and/or CN and/or one or two CH groups may be replaced by N, phenanthrene-2,7-diyl or 9,10-dihydrophenanthrene-2,7diyl, in each of which one, two or more H atoms may be replaced by F and/or one or two CH groups may be replaced by N, indane-2,5-diyl, indan-1-one-2,5-diyl, benzothiazole-2,6-diyl, benzothiazole-2,5-diyl, benzoxazole-2,6-diyl, benzoxazole-2,5-diyl, benzofuran-2,5-diyl, benzofuran-2,6-diyl, 2,3dihydrobenzofuran-2,5-diyl, piperazine-1,4-diyl, piperazine-2,5-diyl, 1-alkyl-1-silacyclohexylene-1,4-diyl or 1,3-dioxaborinane-2,5-diyl;

a, b and c are zero or one,
  with the proviso that the compound of the formula (I) cannot contain more than four five- or multimembered ring systems.

The symbols and indices in the formula (I) are preferably defined as follows-.

R is preferably identical or different and is preferably
  a) hydrogen, —F, —$OCF_3$ or —CN,
  b) a straight-chain or branched alkyl radical (with or without an asymmetrical carbon atom) having 1 to 18 carbon atoms, where
    b1) one or more non-adjacent and non-terminal —$CH_2$— groups may be replaced by —O—, —CO—O—, —O—CO—, —O—CO—O— or —Si(CH$_3$)$_2$—, and/or
    b2) one —$CH_2$— group may be replaced by cyclopropane-1,2-diyl, 1,4-phenylene or trans-1,4-cyclohexylene, and/or
    b3) one or more H atoms may be replaced by F, and/or
    b4) the terminal $CH_3$ group may be replaced by one of the following chiral groups (optically active or racemic):

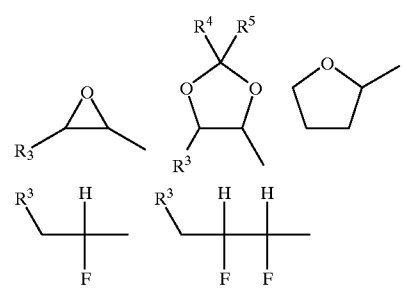

R is particularly preferably identical or different and is particularly preferably
  a) hydrogen,
  b) a straight-chain or branched alkyl radical (with or without an asymmetrical carbon atom) having 1 to 16 carbon atoms, where b1) one or two non-adjacent and non-terminal $CH_2$— groups may be replaced by —O—, —CO—O—, —O—CO—, —O—CO—O— or —Si($CH_3$)$_2$—, and/or b2) one —$CH_2$— group may be replaced by 1,4-phenylene or trans-1,4-cyclohexylene, and/or b3) one or more H atoms may be replaced by F, and/or b4) the terminal $CH_3$ group may be replaced by one of the following chiral groups (optically active or racemic):

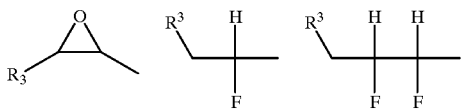

$R^3$, $R^4$, $R^5$, $R^6$ and $R^7$ are preferably identical or different and are preferably a) hydrogen b) a straight-chain or branched alkyl radical (with or without an asymmetrical carbon atom) having 1 to 14 carbon atoms, where b1) one or two non-adjacent and non-terminal $CH_2$— groups may be replaced by —O—, and/or b2) one $CH_2$— group may be replaced by —CH=CH—, c) $R^4$ and $R^5$ together may alternatively be —($CH_2$)$_4$— or —($CH_2$)$_5$— if they are bonded to an oxirane, dioxolane, tetrahydrofuran, tetrahydropyran, butyrolactone or valerolactone system.

$R^3$, $R^4$, $R^5$, $R^6$ and $R^7$ are particularly preferably identical or different and are particularly preferably a) hydrogen b) a straight-chain or branched alkyl radical (with or without an asymmetrical carbon atom) having 1 to 14 carbon atoms, where b1) one non-terminal —$CH_2$— group may be replaced by —O—, c) $R^4$ and $R^5$ together may alternatively be —($CH_2$)$_4$— or —($CH_2$)$_5$— if they are bonded to an oxirane, dioxolane, tetrahydrofuran, tetrahydropyran, butyrolactone or valerolactone system.

$R_f$ is preferably a straight-chain, partially or perfluorinated alkyl radical having 2 to 18 carbon atoms, where a) one or more non-adjacent and non-terminal —$CH_2$— or —$CF_2$— groups may be replaced by —O—, —CO—O— or —O—CO—, and/or b) one —$CH_2$— or —$CF_2$— group may be replaced by —CH=CH—, —C≡C—, cyclopropane-1,2-diyl, 1,4-phenylene, trans-1,4-cyclohexylene or 1,3-cyclopentylene.

$R_f$ is particularly preferably a straight-chain perfluorinated alkyl radical having 4 to 16 carbon atoms, where a) one or two non-adjacent and non-terminal —$CF_2$— groups may be replaced by —O—.

B is preferably

—O—, —($CH_2$)$_{n+1}$—O—, —O—($CH_2$)$_{n+1}$—, —CO—O—($CH_2$)$_n$—, —O—CO—($CH_2$)$_n$—, —CH=CH—, —C≡C—, —($CH_2$)$_{n+1}$—, —O—[($CH_2$)$_{m+1}$—O]$_l$—($CH_2$)$_n$—, —[($CH_2$)$_{m+1}$—O]$_l$—($CH_2$)$_n$— or a single bond.

B is particularly preferably

—O—, —O—($CH_2$)$_n$—, —CO—O—($CH_2$)$_{n-1}$—, —O—CO—($CH_2$)$_{n-1}$—, —($CH_2$)$_n$—, —O—[($CH_2$)$_{m+1}$—O]$_l$—($CH_2$)$_n$— or a single bond.

$M^1$, $M^2$ and $M^3$ are preferably identical or different and are preferably

—CO—O—, —O—CO—, —$CH_2$—O—, —O—$CH_2$—, —CH=CH—, —C≡C—, —$CH_2$—$CH_2$—CO—O—, —O—CO—$CH_2$—$CH_2$— or a single bond.

$M^1$, $M^2$ and $M^3$ are particularly preferably identical or different and are particularly preferably —CO—O—, —O—CO—, —$CH_2$—O—, —O—$CH_2$— or a single bond.

$A^1$, $A^2$, $A^3$ and $A^4$ are preferably identical or different and are preferably 1,4-phenylene, in which one or two H atoms may be replaced by F, Cl, $CH_3$ and/or CN, 1,3-phenylene, pyridine-2,5-diyl, in which one or two H atoms may be replaced by F and/or CN, pyrimidine-2,5-diyl, in which one or two H atoms may be replaced by F and/or CN, trans-1,4-cyclohexylene, in which one or two H atoms may be replaced by CN and/or F, 1,3,4-thiadiazole-2,5-diyl, 1,3-dioxane-2,5-diyl, 1,3-thiazole-2,4-diyl, in which one H atom may be replaced by F, 1,3-thiazole-2,5-diyl, in which one H atom may be replaced by F, thiophene-2,5-diyl, in which one or two H atoms may be replaced by F, naphthalene-2,6-diyl, in which one or two H atoms may be replaced by F and/or CN and/or one or two CH groups may be replaced by N, phenanthrene-2,7-diyl or 9,10-dihydrophenanthrene-2,7-diyl, in each of which one, two or more H atoms may be replaced by F and/or one or two CH groups may be replaced by N, indane-2,5-diyl, benzothiazole-2,6-diyl or benzothiazole-2,5-diyl.

$A^1$, $A^2$, $A^3$ and $A^4$ are particularly preferably identical or different and are particularly preferably 1,4-phenylene, in which one or two H atoms may be replaced by F, Cl and/or CN, 1,3-phenylene, pyridine-2,5-diyl, in which one H atom may be replaced by F, pyrimidine-2,5-diyl, trans-1,4-cyclohexylene, in which one or two H atoms may be replaced by CN and/or F, 1,3,4-thiadiazole-2,5-diyl, 1,3-thiazole-2,5-diyl, thiophene-2,5-diyl, naphthalene-2,6-diyl, in which one or two CH groups may be replaced by N, phenanthrene-2,7-diyl or 9,10-dihydrophenanthrene-2,7-diyl, in each of which one, two or more H atoms may be replaced by F and/or one or two CH groups may be replaced by N, or indane-2,5-diyl.

Very particularly preferred compounds of the formula (I) are those of the formulae (I-1) to (I-64):

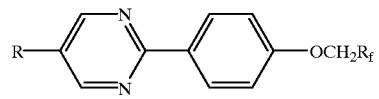

(I-1)

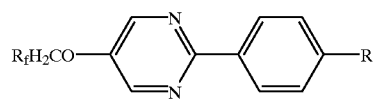

(I-2)

(I-3)
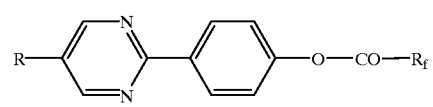
(I-4)
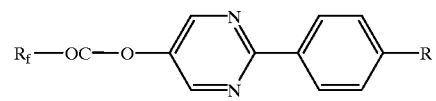
(I-5)
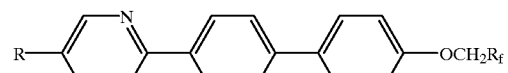
(I-6)
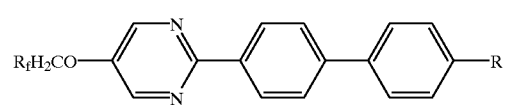
(I-7)
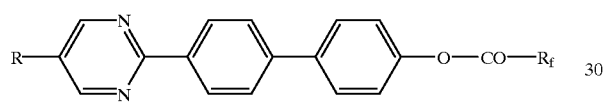
(I-8)
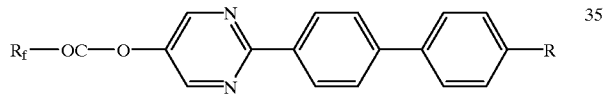
(I-9)
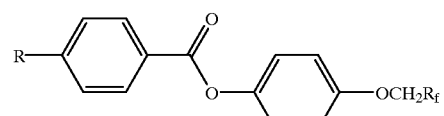
(I-10)
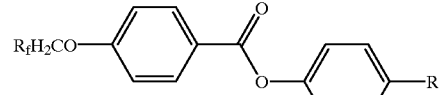
(I-11)
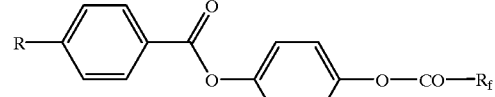
(I-12)
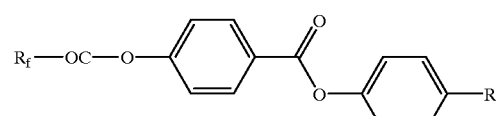
(I-13)
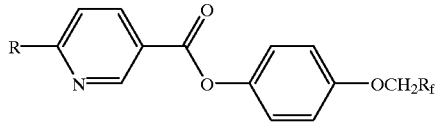
(I-14)
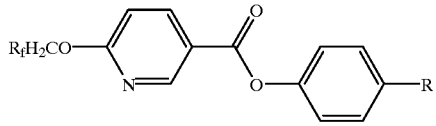
(I-15)
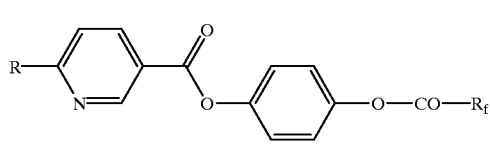
(I-16)
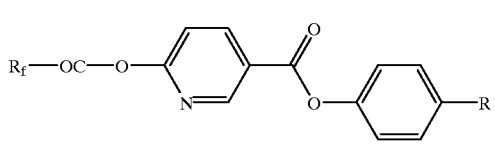
(I-17)
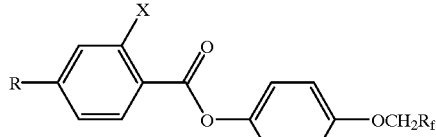
(I-18)
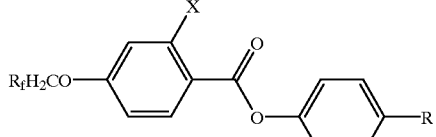
(I-19)
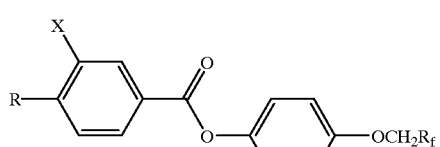
(I-20)
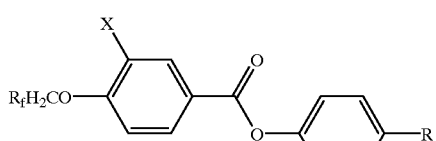
(I-21)
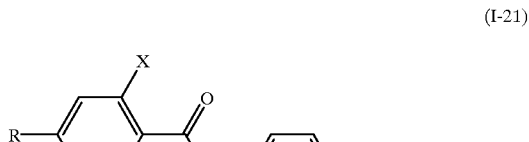

(I-22)
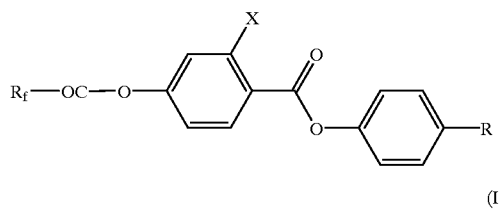
(I-23)
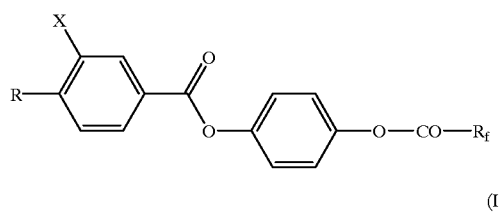
(I-24)
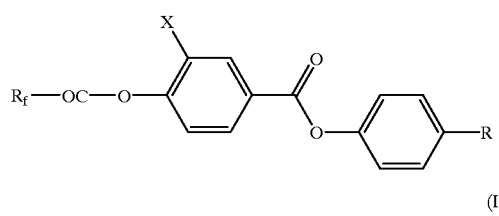
(I-25)
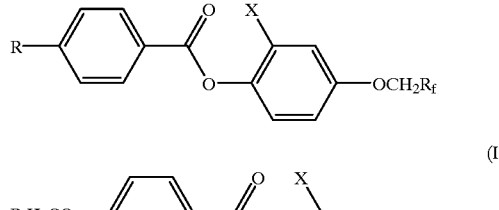
(I-26)
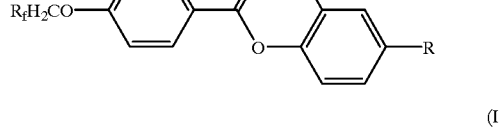
(I-27)
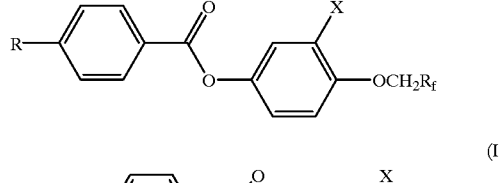
(I-28)
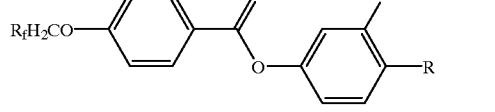
(I-29)
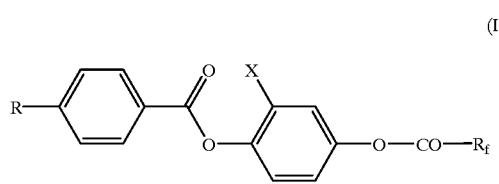
(I-30)
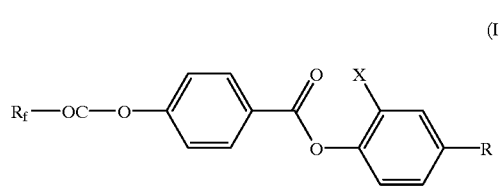
(I-31)
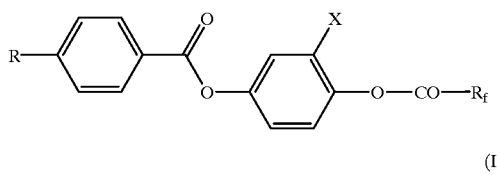
(I-32)
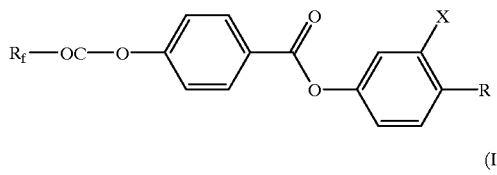
(I-33)
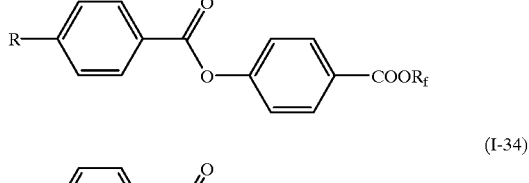
(I-34)
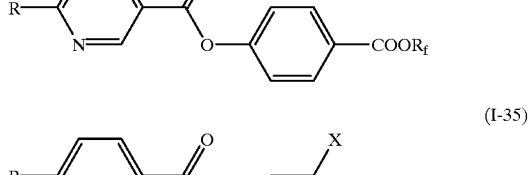
(I-35)
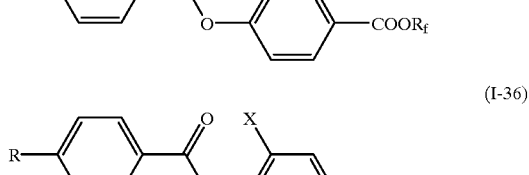
(I-36)
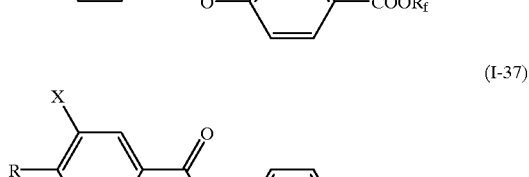
(I-37)
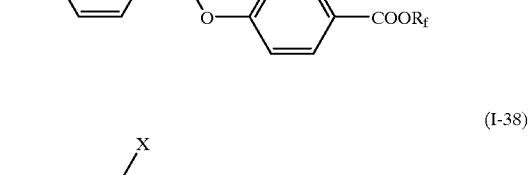
(I-38)
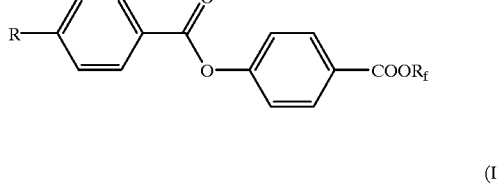
(I-39)
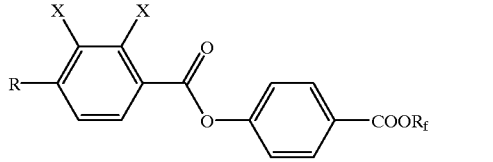

(I-40) 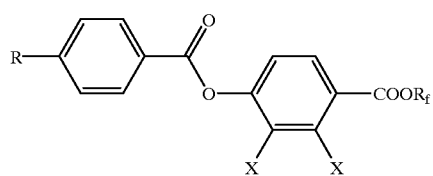
(I-41) 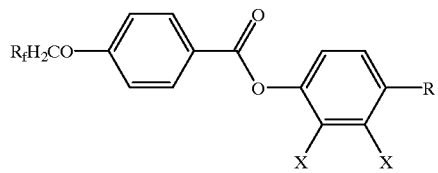
(I-42) 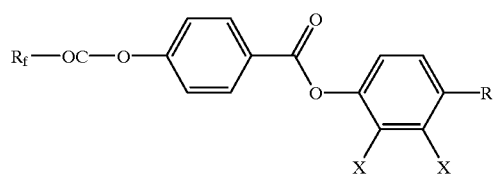
(I-43) 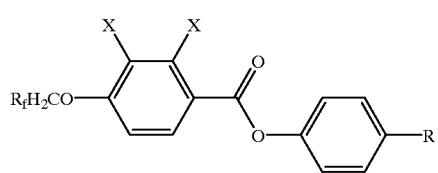
(I-44) 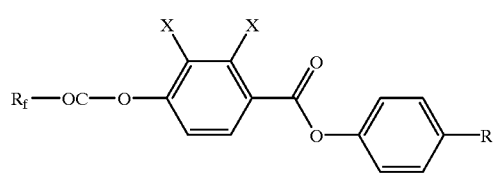
(I-45) 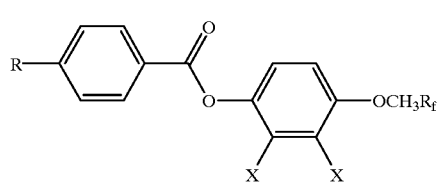
(I-46) 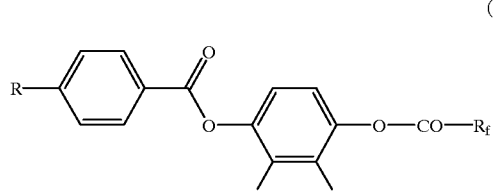
(I-47) 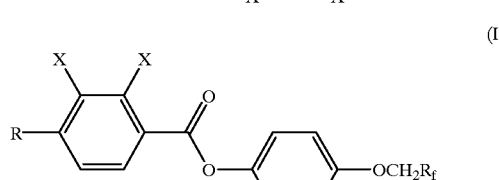
(I-48) 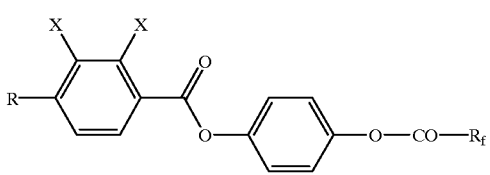
(I-49) 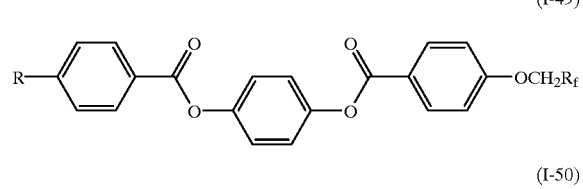
(I-50) 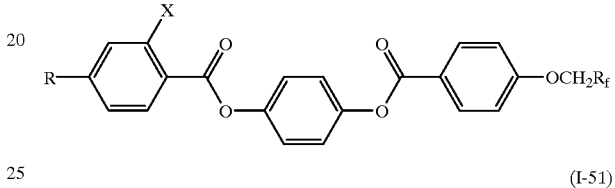
(I-51) 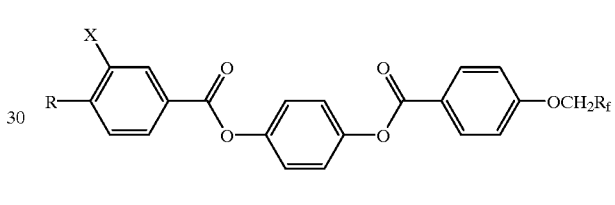
(I-52) 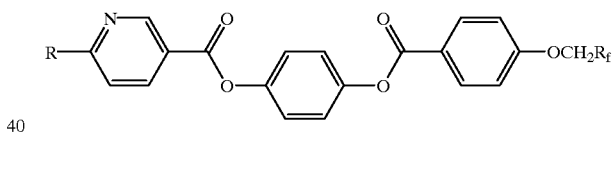
(I-53) 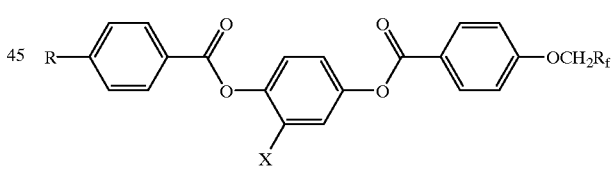
(I-54) 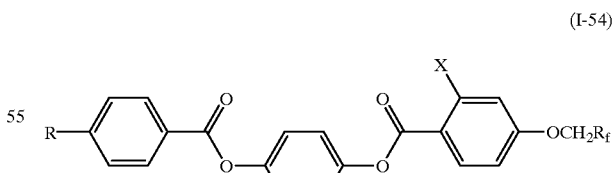
(I-55) 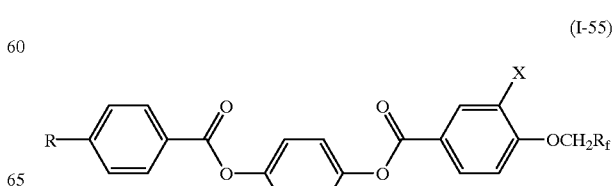

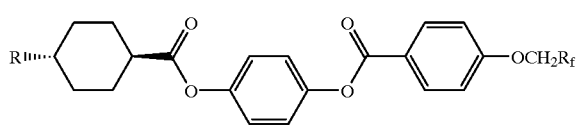
(I-56)

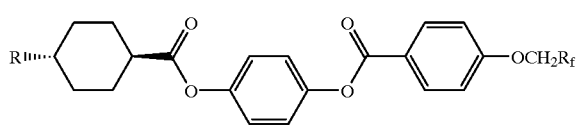
(I-57)

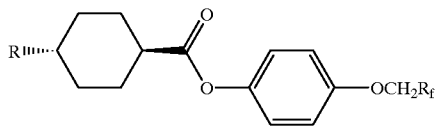
(I-58)

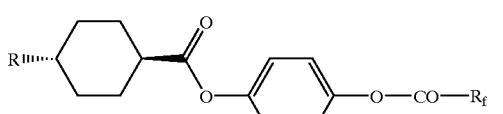
(I-59)

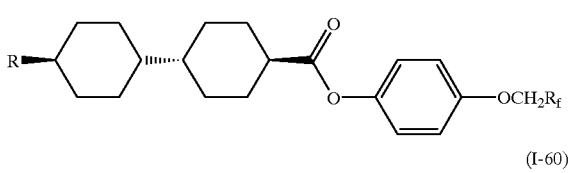
(I-60)

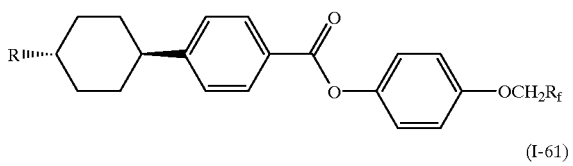
(I-61)

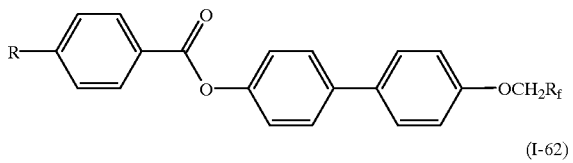
(I-62)

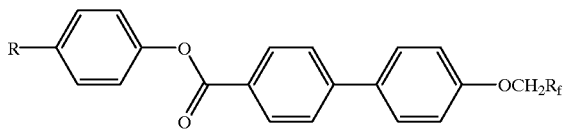
(I-63)

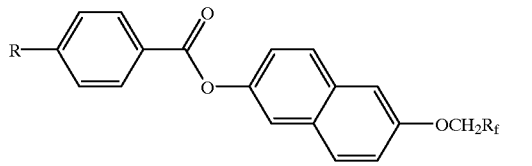
(I-64)

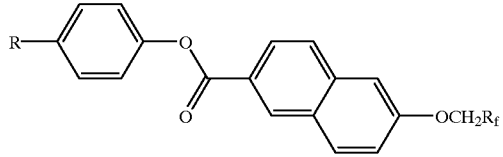

in which X is F, Cl or CN, and R and $R_f$ have the meanings and preferences given for the formula (I).

The FLC mixtures according to the invention consist of at least 2, preferably from 3 to 30, particularly preferably from 4 to 20 components. Of these, at least 2, preferably from 3 to 25, particularly preferably from 4 to 20, are generally compounds of the formula (I).

The mixtures generally comprise at least 5% by weight, preferably at least 20% by weight, particularly preferably at least 50% by weight, of one or more compounds of the formula (I).

The working phase is a chiral tilted phase, preferably the $S_c^*$ phase. The mixtures preferably comprise a non-optically active base mixture, preferably in a proportion of >50%, and one or more optically active compounds (dopants) which may themselves be liquid-crystalline, but need not be liquid-crystalline.

In the service-temperature range, the 'layer leaning' angle, i.e. the angle between smectic layer perpendiculars and the inner surface of the glass or plastic outer plates, is preferably less than half the tilt angle of the ferroelectric liquid-crystal phase.

The layer leaning angle is a measure of the occurrence of a 'chevron', i.e. a kinked structure. It is defined as the angle between the smectic layer perpendiculars and the inner surface of the outer plates of the display. At a layer leaning angle of 0°, a 'bookshelf' arrangement exists, which facilitates very high brightness and very high contrast. In addition, no interfering 'zig-zag' defect lines occur in the display. The smaller the layer leaning angle as defined here, the more perpendicular the smectic layers are to the outer plates and the less a chevron forms. However, if the layer leaning angle is equal to the tilt angle of the smectic phase, a kink forms, i.e. a chevron of maximum pronouncement with minimum brightness and maximum interference by zig-zag defect lines.

The mixtures according to the invention preferably comprise more than 75% by weight of compounds of the formula (I). Further components are preferably mesogenic compounds, in particular smectogenic and/or nematogenic compounds, particularly preferably having thermodynamically stable smectic and/or nematic and/or cholesteric phases.

Such further components are very particularly preferably compounds of the formula (II)

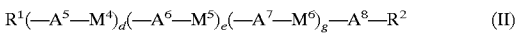 (II)

in which
R$^1$ and R$^2$ are identical or different and, independently of one another, have the same meanings and preferences as R in the formula (I), with the proviso that at most one of the radicals R$^1$ and R$^2$ can be hydrogen, —F, —Cl, —CF$_3$, —OCF$_3$ or —CN, and M$^4$, M$^5$, M$^6$, A$^5$, A$^6$, A$^7$, A$^8$, d, e and g are identical or different and, independently of one another, have the same meanings and preferences as M$^1$, M$^2$, M$^3$, A$^1$, A$^2$, A$^3$, A$^4$, a, b and c respectively in the formula (I).

These include, for example:
derivatives of phenylpyrimidine, as described, for example, in WO 86/06401 and U.S. Pat. No. 4,874,542,
meta-substituted six-membered-ring aromatic compounds, as described, for example, in EP-A 0 578 054,
silicon compounds, as described, for example, in EP-A 0 355 008,
mesogenic compounds having only one side chain, as described, for example, in EP-A 0 541 081,
hydroquinone derivatives, as described, for example, in EP-A 0 603 786, phenylbenzoates and biphenylbenzoates, as described, for example, in P. Keller, Ferroelectrics 1984, 58, 3; Liq. Cryst. 1987, 2, 63; Liq.

Cryst. 1989, 5, 153; and J. W. Goodby et al., Liquid Crystals and Ordered Fluids, Vol. 4, New York, 1984, thiadiazoles, as described, for example, in EP-A 0 309 514, biphenyls, as described, for example, in EP-A 0 207 712 or Adv. Liq. Cryst. Res. Appl. (Ed. Bata, L.) 3 (1980), phenylpyridines, as described, for example, in Ferroelectrics 1996, 180, 269, or Liq. Cryst. 1993, 14, 1169, benzanilides, as described, for example, in Liq. Cryst. 1987, 2, 757, or Ferroelectrics 1984, 58, 81, terphenyls, as described, for example, in Mol. Cryst. Liq. Cryst. 1991, 195, 221; WO 89/02425 or Ferroelectrics 1991, 114, 207, 4-cyanocyclohexyls, as described, for example, in Freiburg Congress on Liquid Crystals 1986, 16, V8, 5-alkylthiophenecarboxylic esters, as described, for example, in Butcher, J. L., disseration, Nottingham 1991, and 1,2-diphenylethanes, as described, for example, in Liq. Cryst. 1991, 9, 253.

Examples of chiral, non-racemic dopants are the following:

optically active phenylbenzoates, as described, for example, in P. Keller, Ferroelectrics 1984, 58, 3, and J. W. Goodby et al., Liquid Crystals and Ordered Fluids, Vol. 4, New York, 1984, optically active oxirane ethers, as described, for example, in EP-A 0 263 437 and WO-A 93/13093, optically active oxirane esters, as described, for example, in EP-A 0 292 954, optically active dioxolane ethers, as described, for example, in EP-A0351 746, optically active dioxolane esters, as described, for example, in EP-A 0 361 272, optically active tetrahydrofuran-2-carboxylic esters, as described, for example, in EP-A 0 355 561, optically active 2-fluoroalkyl ethers, as described, for example, in EP-A 0 237 007, EP-A 0 428 720 and U.S. Pat. No. 5,051,506, and optically active α-halocarboxylic esters, as described, for example, in U.S. Pat. No. 4,855,429.

Particularly preferred components of the formula (I) are those in Groups A to M:

A. Phenylpyrimidine derivatives of the formula (III)

$$R^1—A^1—A^2—R^2 \quad (III)$$

in which $R^1$ and $R^2$ are each alkyl having 1–15 carbon atoms, in which, in addition, one or two non—adjacent $CH_2$— groups may be replaced by —O—, —S—, —Co—, —O—CO—, —CO—O—, —O—CO—O—, —CO—S—, —S—CO—, —CHHalogen—, —CHCN—and/or —CH=CH—, $A^1$ is 1,4-phenylene, trans—1,4—cyclohexylene or a single bond, and $A^2$ is

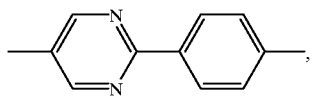,

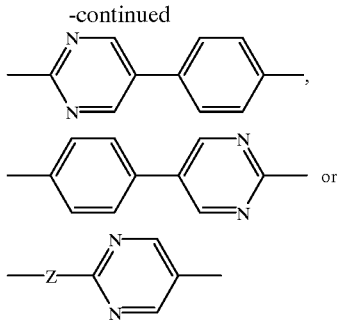

where

Z is —O—CO—, —CO—O—, —S—CO—, —CO—S—, —$CH_2$O—, —O$CH_2$— or —$CH_2CH_2$—.

B. Compounds having only one side chain, of the formula (IV)

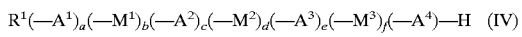

in which:

$R^1$ is a straight-chain or branched alkyl radical having 1 to 22 or 3 to 22 carbon atoms respectively, in which one or two non—adjacent and non-terminal $CH_2$— groups may also be replaced by —O—, —CO—, —CO—O—, —O—CO—, —O—CO—O— or —Si$(CH_3)_2$—, $A^1$, $A^2$, $A^3$ and $A^4$ are identical or different and are 1,4-phenylene, in which one or two H atoms may be replaced by F or CN, pyridine-2,5-diyl, in which one or two H atoms may be replaced by F, pyrimidine-2,5-diyl, in which one or two H atoms may be replaced by F, trans—1,4—cyclohexylene, 1,3,4-thiadiazole-2,5-diyl or naphthalene-2,6-diyl, $M^1$, $M^2$ and $M^3$ are identical or different and are —CO—O—, —O—CO—, —$CH_2$—O—, —O—$CH_2$— or —$CH_2$—$CH_2$—, a, b, c, d, e and f are zero or one, with the proviso that the sum a+c+e is 0, 1, 2 or 3.

C. Meta-substituted compounds of the formula (V)

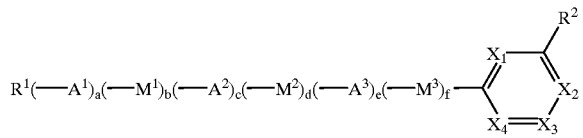

in which $R^1$ and $R^2$ are identical or different and are
a straight-chain or branched alkyl radical having 1 to 22 or 3 to 22 carbon atoms respectively, in which, in addition, one or two non-adjacent and non-terminal $CH_2$— groups may be replaced by —O—,—CO—, —CO—O—, —O—CO—, —O—CO—O— or —Si$(CH_3)_2$—, $A^1$, $A^2$ and $A^3$ are identical or different and are
1,4-phenylene, in which one or two H atoms may be replaced by F, pyridine-2,5-diyl, in which one or two H atoms may be replaced by F, pyrimidine-2,5-diyl, in which one or two H atoms may be replaced by F, trans-1,4-cyclohexylene, in which one or two H atoms may be replaced by —CN and/or —$CH_3$, or 1,3,4-thiadiazole-2,5diyl, and $A^1$ is alternatively

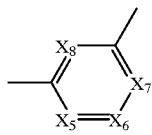

$M^1$, $M^2$ and $M^3$ are identical or different and are —O—, —CO—O—, —O—CO—, —CH$_2$—O—, —O—CH$_2$— or —CH$_2$—CH$_2$—, $X^1$, $X^2$, $X^3$, $X^{4,X5}$, $X^6$, $X^7$ and $X^8$ are CH or N, the number of N atoms per six—membered ring being 0, 1 or 2, a, b, c, d, e and f are zero or one, with the proviso that the sum a+c+e is 0, 1, 2 or 3.

D. Silicon compounds of the formula (VI)

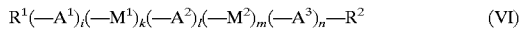

(VI)

in which $R^1$ is a straight-chain or branched alkyl radical having 1 to 22 or 3 to 22 carbon atoms respectively, in which, in addition, one or two non-adjacent and non-terminal CH$_2$— groups may be replaced by —O—, —CO—, —CO—O—, —O—CO— or —O—CO—O—, $R^2$ is a straight-chain or branched alkyl radical having 1 to 22 or 3 to 22 carbon atoms respectively, in which, in addition, one or two non-adjacent and non-terminal CH$_2$— groups may be replaced by —O—, —CO—, —CO—O—, —O—CO— or —O—CO—O—, with the proviso that one CH$_2$ group not bonded to oxygen is replaced by —Si(CH$_3$)$_2$—, $A^1$, $A^2$ and $A^3$ are identical or different and are 1,4-phenylene, in which one or two H atoms may be replaced by F, trans-1,4-cyclohexylene, pyridine-2,5-diyl, in which one or two H atoms may be replaced by F, pyrimidine-2,5-diyl, in which one or two H atoms may be replaced by F, or 1,3,4-thiadiazole-2,5-diyl, $M^1$ and $M^2$ are identical or different and are —CO—O—, —O—CO—, —CH$_2$—O— or —O—CH$_2$—, i, k, l, m and n are zero or 1, with the proviso that i+l+n2 or 3.

E. Hydroquinone derivatives of the formula (VII)

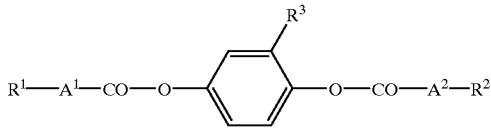

(VII)

in which $R^1$ and $R^2$ are identical or different and are a straight-chain or branched alkyl radical having 1 or 3 to 16 carbon atoms, preferably 1 or 3 to 10 carbon atoms respectively, in which, in addition, one or two non-adjacent and non-terminal CH$_2$— groups may be replaced by —O—, —CO—, —O—CO—, —CO—O— or —O—CO—O—, preferably —O—, —O—CO— or —CO—O—, $R^3$ is —CH$_3$, —CF$_3$ or —C$_2$H$_5$, preferably —CH$_3$ or —CF$_3$, $A^1$ and $A^2$ are identical or different and are 1,4-phenylene or trans-1,4-cyclohexylene, preferably 1,4-phenylene.

F. Pyridylpyrimidines of the formula (VIII)

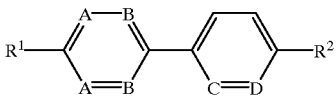

(VIII)

in which

A is N and B is CH or A is CH and B is N, C is N and D is CH or C is CH and D is N, where one or two CH groups may be replaced by CF groups, $R^1$ and $R^2$ are identical or different and are a straight-chain or branched alkyl radical having 1 to 22 or 3 to 22 carbon atoms respectively, in which, in addition, one or two non-adjacent and non-terminal CH$_2$— groups may be replaced by —O—, —CO—, —CO—O—, —O—CO— or —O—CO—O—.

G. Phenylbenzoates of the formula (IX)

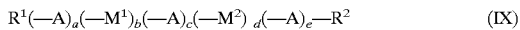

(IX)

in which $R^1$ and $R^2$ are identical or different and are a straight-chain or branched alkyl radical having 1 to 22 or 3 to 22 carbon atoms respectively, in which, in addition, one or two non-adjacent and non-terminal CH$_2$— groups may be replaced by —O—, —CO—, —CO—O—, —O—CO— or —O—CO—O—, A is 1,4-phenylene, $M^1$ and $M^2$ are identical or different and are —CO—O— or —O—CO—, a, b, c, d and e are zero or one, with the proviso that a+c+e=2 or 3 and b+d=1 or 2.

H. Optically active phenylbenzoates of the formula (X)

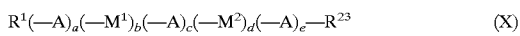

(X)

in which $R^1$ and $R^2$ are identical or different and are a straight-chain or branched alkyl radical having 1 to 22 or 3 to 22 carbon atoms respectively, in which, in addition, one or two non-adjacent and non-terminal CH$_2$— groups may be replaced by —O—, —CO—, —CO—O—, —O—CO— or —O—CO—O—, and in which at least one of the radicals $R^1$ and $R^2$ is a branched, optically active alkyl group, A is 1,4-phenylene, $M^1$ and $M^2$ are identical or different and are —CO—O—, —O—CO— or a single bond, and a, b, c, d and e are zero or one, with the proviso that a+c+e=2 or 3 and b+d=1 or 2.

I. Optically active oxirane ethers of the formula (XI)

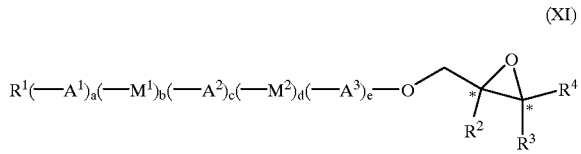

(XI)

in which the symbols and indices are defined as follows:

\* is a center of chirality, $R^1$ is a straight-chain or branched alkyl radical having 1 to 22 or 3 to 22 carbon atoms respectively, in which, in addition, one or two non-adjacent and non-terminal CH$_2$— groups may be replaced by —O—, —CO—, —CO—O—, —O—CO—, —O—CO—O— or —Si(CH$_3$)$_2$—, or the following optically active group,

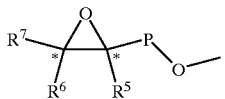

R$^2$, R$^3$, R$^4$, R$^5$, R$^6$ and R$^7$ are identical or different and are hydrogen or a straight-chain or branched alkyl radical having 1 to 16 carbon atoms, P is —CH$_2$— or —CO—, A$^1$, A$^2$ and A$^3$ are identical or different and are 1,4-phenylene, in which one or two H atoms may be replaced by F, pyridine-2,5-diyl, in which one or two H atoms may each be replaced by F, pyrimidine-2,5-diyl, in which one or two H atoms may be replaced by F, trans-1,4-cyclohexylene, in which one or two H atoms may be replaced by —CN and/or —CH$_3$, or 1,3,4-thiadiazole-2,5-diyl, M$^1$ and M$^2$ are identical or different and are —CO—O—, —O—CO—, —CH$_2$—O—, —O—CH$_2$— or —CH$_2$—CH$_2$—, and a, b, c, d and e are zero or one.

The asymmetrical carbon atoms in the oxirane ring or rings can have identical or different R or S configurations.

J. Optically active oxirane esters of the formula (XII)

(XII)

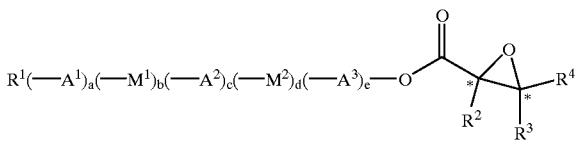

in which the symbols and indices are defined as follows:

* is a center of chirality,

R$^1$ is a straight-chain or branched alkyl radical having 1 to 22 or 3 to 22 carbon atoms respectively, in which, in addition, one or two non-adjacent and non-terminal CH$_2$— groups may be replaced by —O—, —CO—, —CO—O—, —O—CO—, —O—CO—O— or —Si(CH$_3$)$_2$—, R$^2$, R$^3$ and R$^4$ are identical or different and are hydrogen or a straight-chain or branched alkyl radical having 1 to 16 carbon atoms, A$^1$, A$^2$ and A$^3$ are identical or different and are 1,4-phenylene, in which one or two H atoms may be replaced by F, pyridine-2,5-diyl, in which one or two H atoms may each be replaced by F, pyrimidine-2,5-diyl, in which one or two H atoms may be replaced by F, trans-1,4-cyclohexylene, in which one or two H atoms may be replaced by —CN and/or —CH$_3$, or 1,3,4-thiadiazole-2,5-diyl, M$^1$ and M$^2$ are identical or different and are —CO—O—, —O—CO—, —CH$_2$—O—, —O—CH$_2$— or —CH$_2$—CH$_2$—, and a, b, c, d and e are zero or one.

The asymmetrical carbon atoms in the oxirane ring can have identical or different R or S configurations.

K. Optically active dioxolane ethers of the formula (XIII)

(XIII)

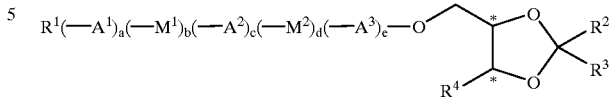

in which the symbols and indices are defined as follows:

* is a center of chirality,

R$^1$ is a straight-chain or branched alkyl radical having 1 to 22 or 3 to 22 carbon atoms respectively, in which, in addition, one or two non-adjacent and non-terminal CH$_2$— groups may be replaced by —O—, —CO—, —CO—O—, —O—CO—, —O—CO—O— or —Si(CH$_3$)$_2$—, R$^2$, R$^3$ and R$^4$ are identical or different and are hydrogen, a straight-chain or branched alkyl radical having 1 to 16 or 3 to 10 carbon atoms respectively or an alkenyl radical having 2 to 16 carbon atoms, where R and R together may alternatively be —(CH$_2$)$_5$—, A$^1$, A$^2$ and A$^3$ are identical or different and are 1,4-phenylene, in which one or two H atoms may be replaced by F, pyridine-2,5diyl, in which one or two H atoms may be replaced by F, pyrimidine-2,5-diyl, in which one or two H atoms may be replaced by F, trans-1,4-cyclohexylene, in which one or two H atoms may be replaced by —CN and/or —CH$_3$, or 1,3,4-thiadiazole-2, 5-diyl, M$^1$ and M$^2$ are identical or different and are —CO—O—, —O—CO—, —CH$_2$—O—, —O—CH$_2$— or —CH$_2$—CH$_2$—, and a, b, c, d and e are zero or one.

Asymmetrical carbon atoms in the dioxolane ring can have identical or different R or S configurations.

L. Optically active dioxolane esters of the formula (XI)

(XIV)

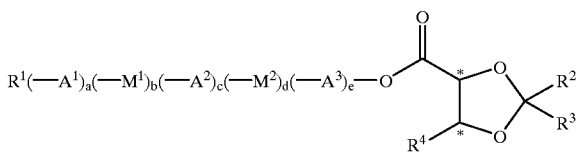

in which the symbols and indices are defined as follows:

* is a center of chirality,

R$^1$ is a straight-chain or branched alkyl radical having 1 to 16 or 3 to 16 carbon atoms respectively, in which, in addition, one or two non-adjacent and non-terminal CH$_2$ groups may be replaced by —O—, —CO—, —O—CO— or —CO—O—, R$^2$, R$^3$ and R$^4$ are identical or different and are hydrogen or an alkyl or alkenyl radical having 1 to 10 or 2 to 10 carbon atoms respectively, where R$^2$ and R$^3$ together may alternatively be —(CH$_2$)$_5$—, A$^1$, A$^2$ and A$^3$ are identical or different and are 1,4-phenylene, in which one or two H atoms may be replaced by F, pyridine-2,5-diyl, in which one or two H atoms may be replaced by F, pyrimidine-2,5-diyl, in which one or two H atoms may be replaced by F, trans-1,4-cyclohexylene, in which one or two H atoms may be replaced by —CN and/or —CH$_3$, or 1,3,4-thiadiazole-2,5-diyl, M$^1$ and M$^2$ are identical or different and are —CO—O—, —O—CO—, —CH$_2$—O—, —O—CH$_2$— or —CH$_2$—CH$_2$—, and a, b, c, d and e are zero or one.

Asymmetrical carbon atoms in the dioxolane ring can have identical or different R or S configurations.

M. Macrocyclic compounds of the formula (XV)

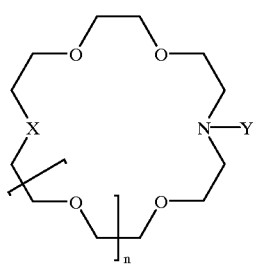

(XV)

in which n is 0 or 1,

Y is —CO—(t-butyl), —CO—(adamantyl) or —CO-alkyl, and

X is —O— or —N(Y)—.

The liquid-crystal components of the formulae (I) to (XV) are prepared by methods known per se which are familiar to the person skilled in the art, as described, for example, in Houben-Wehl, Methoden der organischen Chemie [Methods of Organic Chemistry], Georg Thieme Verlag, Stuttgart, or the publications cited therein.

In particular, the preparation of compounds of the formula (I) is described, for example, in E. P. Janulis et al., Ferroelectrics 1988, 85, 375–384; H. T. Nguyen et al., Liq. Cryst. 1991, 10, 389; S. Misaki et al., Mol. Cryst. Liq. Cryst. 1981, 66, 123–132; L. M. Yagupolski et al., Mol. Cryst. Liq. Cryst. 1980, 56 (Letters), 209–215; A. V. lvashchenko et al., Mol. Cryst. Liq. Cryst. 1981, 67, 235–240; H. Liu, H. Nohira, Liq. Cryst. 1996, 20, 581–586; ibid. 1997, 22, 217–222; EP—B 255 236; WO 91/00897; WO 93/22396; WO 96/15092.

The mixtures can be prepared by methods known per se.

The display according to the invention contains polarizers, electrodes, for example made of indium—tin oxide, substrates made of plastic or thin glass which have been provided with an alignment layer and possibly further functional layers (passivation, diffusion barrier, insulation, antireflection layers, etc.), a liquid-crystal layer and active thin-film elements. The latter include the possible types aSi-TFT, pSi-TFT, diodes and metal-insulator-metal (MIM) elements. The display according to the invention can also be of the in-plane switching LCD or AM-ECB type or an active—matrix liquid-crystal display which operates in a similar way (see, for example, C. Prince, Seminar Lecture Notes, Volume 1, p. M—3/3—M—3/22, SID International Symposium 1997, Boston, USA; B. B. Bahadur, Liquid Crystals Application and Uses, Vol. 1, pp.410, World Scientific Publishing, 1990; E. Luder, Recent Progress of AMLCD's, Proceedings of the 15th International Display Research Conference, 1995, p.9-p.12).

In addition, such displays can advantageously have electrode separations of greater than 1.5 μm, in particular greater than 1.8 μm, and can nevertheless be operated at low voltages of below 30 volts. The large electrode separation compared with the FLC displays cited hitherto allows a high yield in production.

The display according to the invention can be addressed as described in detail in the relevant literature (see, for example, C. Prince, Seminar Lecture Notes, Volume 1, p. M-313-M-3/22, SID International Symposium 1997, Boston, USA, or T. Tsukuda, see above).

Of crucial importance for the electro—optical properties and storage properties of the display is the approximately 1–3 μm thick FLC layer, whose layer thickness is preferably fixed by spacers. These spacers can be incorporated particles, such as beads, or structured columns in the interior of the display.

The entire cell, which is usually sealed by means of an adhesive frame, can be provided with electrical contacts, for example by soldering, bonding, pressing or the like.

The electro-optical effect, which is preferably based on the birefringence of the FLC material or on the dielectric anisotropy of an incorporated dichroic dye, becomes visible between crossed polarizers (polarizing foils) or a polarizer ('guest-host' mode, reflective mode).

The FLC display according to the invention can be produced by processes known in principle, as described, for example, in Tsukuda.

References cited in this application are expressly incorporated herein.

The invention is explained in greater detail by the examples, without this being intended to represent a limitation.

EXAMPLES

Example 1

Synthesis of 2-4[2,2-difluoro-2-(1,1,2,2-tetrafluoro-2-nonafluorobutoxy-ethoxy)ethoxy]phenyl}-5-octyloxypyrimidine

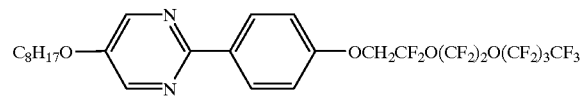

A suspension of sodium hydride in dry dimethylformamide is introduced, and a solution of 2-{4-[2,2-difluoro-2-(1,1,2,2-tetrafluoro-2-nonafluoro-butoxyethoxy)ethoxy]phenyl}pyrimidin-5-ol (obtained by Williamson etherification of 5-benzyloxy-2—(4-hydroxyphenyl)pyrimidine using 2,2-difluoro-2-(1,1,2,2-tetrafluoro-2-nonafluorobutoxyethoxy)ethyl toluene-4-sulfonate followed by hydrogenation) in the same solvent is added dropwise at 0° C. The mixture is stirred at room temperature until the evolution of gas is complete, and the equivalent amount of 1—bromooctane is then added dropwise. The mixture is warmed for 4–6 hours at about 60° C. The reaction mixture is cooled, poured into ice-water, and extracted a number of times with dichloromethane. The combined organic extracts are washed with saturated sodium chloride solution and dried using sodium sulfate. The solvent is removed under reduced pressure, and the crude product is purified by column chromatography on silica gel and purified by recrystallization from ethanol. Phase transitions (in ° C.): X 45 $S_C$ 81 $S_A$ 94 I.

Example 2

Mixture example

| Component | Prop. by wt. [%] |
|---|---|
| C8H17–[pyrimidine]–[phenyl]–OCH2CF2O(CF2)2OC4F9 | 0.41 |
| C8H17–[pyrimidine]–[phenyl]–OCH2(CF2)3O(CF2)4OC4F9 | 1.25 |
| C8H17–[pyrimidine]–[phenyl]–OCH2CF2O(CF2)2O(CF2)2OCF3 | 0.41 |
| C8H17–[pyrimidine]–[phenyl]–OCH2CF2OC2F5 | 4.5 |
| C10H21–[pyrimidine]–[phenyl]–OCH2CF2O(CF2)2OC4F9 | 0.41 |
| C10H21–[pyrimidine]–[phenyl]–OCH2CF2O(CF2)2OC6F13 | 0.41 |
| C10H21–[pyrimidine]–[phenyl]–OCH2(CF2)3O(CF2)4OC4F9 | 4.91 |
| C8H17O–[pyrimidine]–[phenyl]–OCH2CF2O(CF2)2OC4F9 | 13.5 |
| C8H17O–[pyrimidine]–[phenyl]–OCH2CF2O(CF2)2OC6F13 | 5.8 |
| C8H17O–[pyrimidine]–[phenyl]–OCH2(CF2)3O(CF2)4OC4F9 | 9.2 |
| C9H19O–[pyrimidine]–[phenyl]–OCH2CF2O(CF2)2OC4F9 | 13.5 |
| C10H21O–[pyrimidine]–[phenyl]–OCH2CF2O(CF2)2OC4F9 | 4.5 |

| Component | Prop. by wt. [%] |
|---|---|
| 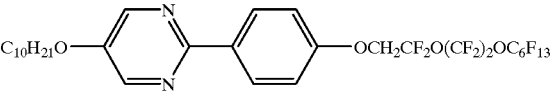 | 13.5 |
| 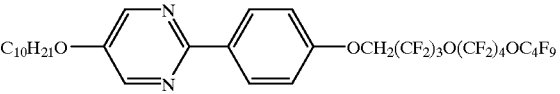 | 8.9 |
| 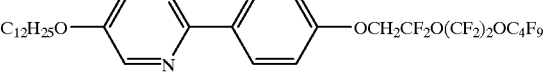 | 4.5 |
| 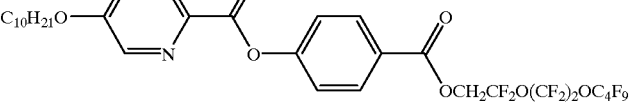 | 4.4 |
| 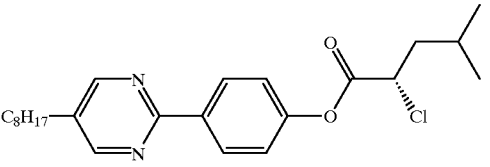 | 6.6 |
| 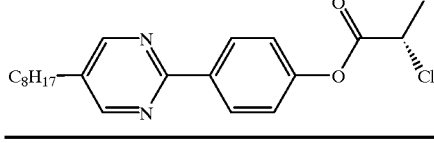 | 3.3 |

What is claimed is:

1. A ferroelectric active- matrix liquid-crystal display containing a ferroelectric liquid crystal containing one or more mesogenic compounds having a partially or perfluorinated side chain of the formula (I)

$$R(-A^1-M^1)_a(-A^2-M^2)_b-(-A^3-M^3)_c-A^4-B-R_f \qquad (I)$$

where the symbols and indices are defined as follows:

R is
  a) hydrogen, —F, —Cl, —CF$_3$, —OCF$_3$ or —CN,
  b) a straight-chain or branched alkyl radical (with or without an asymmetrical carbon atom) having 1 to 20 carbon atoms, where
    b1) one or more non-adjacent and non-terminal CH$_2$— groups may be replaced by —O—, —S—, —CO—, —CO—O—, —O—CO—, —O—CO—O— or —Si(CH$_3$)$_2$—, and/or
    b2) one or more CH$_2$— groups may be replaced by —CH=CH—, —C≡C—, cyclopropane-1,2-diyl, 1,4-phenylene, 1,4-cyclo-hexylene or 1,3-cyclopentylene, and/or
    b3) one or more H atoms may be replaced by F, CN and/or Cl, and/or
    b4) the terminal CH$_3$ group may be replaced by one of the following chiral groups (optically active or racemic):

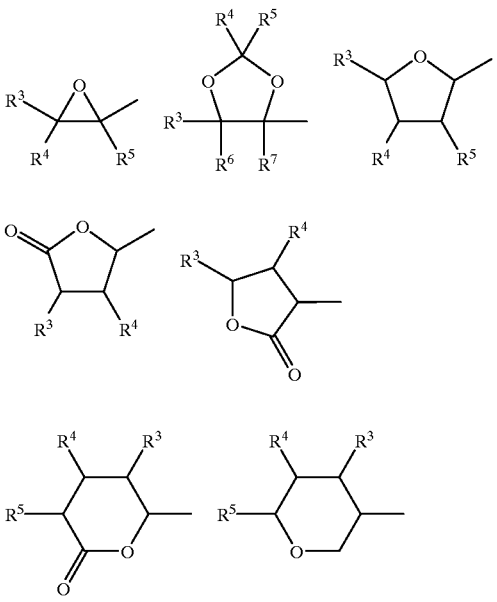

-continued

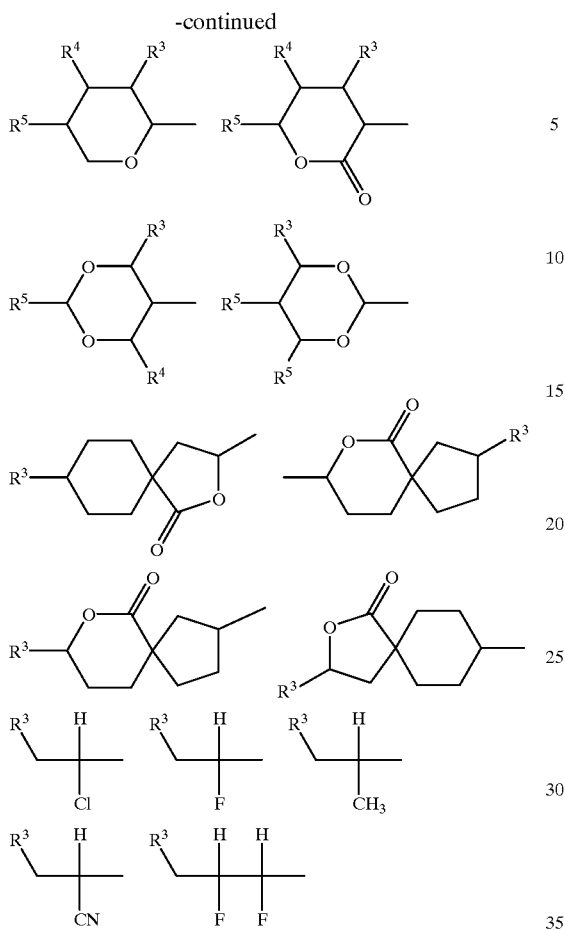

c) B-R$_f$

R$^3$, R$^4$, R$^5$, R$^6$ and R$^7$ are identical of different and are
a) hydrogen
b) a straight-chain or branched alkyl radical (with or without an asymmetrucal carbon atom) having 1 to 16 carbon atoms, where
b1) one or more non-adjacent and non-terminal CH$_2$— groups may be replaced by —O—, and/or
b2) one or two CH$_2$— groups may be replaced by —CH=CH—,
c) R$^4$ and R$^5$ together may alternatively be —CH$_2$)$_4$— or —(CH$_2$)$_5$— if they are bonded to an oxirane, dioxolane, tetrahydrofuran, tetrahydropyran, butyrolactone or valerolactone system;

R$_f$
a straight-chain or branched, partially or perfluorinated alkyl radical (with or without an asymmetrical carbon atom) having 1 to 20 carbon atoms, where
a) one or more non-adjacent and non-terminal CH$_2$— or CF$_2$— groups may be replaed by —O—, —S—, —CO—, —CO—O—, —O—CO—, —O—CO—O— or —Si(CH$_3$)$_2$—, and/or
b) one or more CH$_2$— or CF$_2$— groups may be replaced by —CH=CH—, —C≡C—, cyclopropane-1,2-diyl, 1,4-phenylene, 1,4-cyclohexylene or 1,3-cyclopropane;

B is
—O—, —S—, —(CH$_2$)$_{n+1}$—O—, —O—(CH$_2$)$_{n+1}$—, —(CH$_2$)$_{n+1}$—S—, —S—(CH$_2$)$_{n+1}$—, -CO-(CH$_2$)$_n$—, —CS—O—(CH$_2$)$_n$—, —O—CS—(CH$_2$)$_n$—, —SO$_2$—(CH$_2$)$_n$—, —OSO$_2$—(CH$_2$)$_n$—, —CH=CH—, —C≡C—, —(CH$_2$)$_{n+1}$—, —CH=N—, —N(C$_k$H$_{2k+1}$)—, —(CH$_2$)$_n$—N(C$_k$H$_{2k+1}$)—CO—, —(CH$_2$)$_n$—N(C$_k$H$_{2k+1}$)—SO$_2$—, —O—[(CH$_2$)$_{m+1}$—O]$_l$—(CH$_2$)$_n$—, —[(CH$_2$)$_{m+1}$—O ]$_l$—(CH$_2$)$_n$— or a single bond;

m and n are identical or different and are, independently of one another, an integer from 0 to 15, k is an integer from 0 to 4, and I is an integer from 1 to 6, with the proviso that m+n≦15;

M$^1$, M$^2$ and M$^3$ are identical or different and are
—CO—O—, —O—CO—, —CO—S—, —S—CO—, —CS—O—, —O—CS—, —CS—S—, —S—CS—, —CH$_2$—O—, —O—CH$_2$—, —CH$_2$—S—, —S—CH$_2$—; —CH$_2$—CH$_2$—, —CH=CH—, —C≡C—, —CH$_2$—CH$_2$—CO—O—, —O—CO—CH$_2$—CH$_2$—, —CH=N—or a single bond;

A$^1$, A$^2$, A$^3$ and A$^4$ are identical or different and are 1,4-phenylene, in which one or more H atoms may be replaced by F, Cl, CH$_3$, C$_2$H$_5$, OCH$_3$, CF$_3$, OCF$_3$ and/or CN, 1,3-phenylene, in which one or two CH groups may be replaced by N, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, 1,4-cyclohexylene, in which one or two H atoms may be replaced by CN and/or CH$_3$ and/or F, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4-diyl, in which one H atom may be replaced by F, Cl and/or CN, thiophene-2,5-diyl, in which one or two H atoms may be replaced by F, Cl and/or CN, naphthaene 2,6-diyl, naphthalene-1,4-diyl or naphthalene-1,5-diyl, in each of which one or more H atoms may be replaced by F, Cl and/or CN and/or one or two CH groups may be replaced by N, phenanthrene-2,7-diyl or 9,10-dihydrophenanthrene-2,7-diyl, in each of which one, two or more H atoms may be replaced by F and/or one or two CH groups may be replaced by N, indane-2,5-diyl, indan-1-one-2,5-diyl, benzothiazole-2,6-diyl, benzothiazole-2,5-diyl, benzoxazole-2,6-diyl, benzoxazole-2,5-diyl, benzofuran-2,5-diyl, benzofuran-2,6-diyl, 2,3-dihydrobenzofuran-2,5-diyl, piperazine-1,4-diyl, piperazine-2,5-diyl, 1- alkyl-1-silacyclohexylene-1,4-diyl or 1,3-dioxaborinane-2,5-diyl;

a, b and c are zero or one, with the proviso that the compound of the formula (I) cannot contain more than four five- or multimembered ring systems.

2. A ferroelectric active matrix display according to claim 1, wherein the display has electrodes spaced at least 1.5 μm and which can be switched at voltages of less or equal 30 v.

3. A ferroelectric active matrix display according to claim 1, wherein a liquid crystal mixture of 3 to 30 components is employed of which 3 to 25 components are compounds of the formula (I).

* * * * *